(12) United States Patent
Jeon et al.

(10) Patent No.: US 11,304,859 B2
(45) Date of Patent: Apr. 19, 2022

(54) DIAPER INCLUDING REMOVABLE WAISTBAND

(71) Applicant: DADDY FOR BEBE CO., LTD., Seoul (KR)

(72) Inventors: Young Seok Jeon, Goyang-si (KR); Young Jun Lee, Seoul (KR)

(73) Assignee: DADDY FOR BEBE CO., LTD., Seoul (KR)

( * ) Notice: Subject to any disclaimer, the term of this patent is extended or adjusted under 35 U.S.C. 154(b) by 883 days.

(21) Appl. No.: 16/086,568

(22) PCT Filed: Sep. 26, 2017

(86) PCT No.: PCT/KR2017/010625
§ 371 (c)(1),
(2) Date: Sep. 19, 2018

(87) PCT Pub. No.: WO2019/013391
PCT Pub. Date: Jan. 17, 2019

(65) Prior Publication Data
US 2021/0177674 A1    Jun. 17, 2021

(30) Foreign Application Priority Data

Jul. 10, 2017   (KR) .......................... 10-2017-0087105

(51) Int. Cl.
*A61F 13/15* (2006.01)
*A61F 13/56* (2006.01)
*A61F 13/49* (2006.01)

(52) U.S. Cl.
CPC ...... *A61F 13/5655* (2013.01); *A61F 2013/49087* (2013.01); *A61F 2013/5677* (2013.01)

(58) Field of Classification Search
CPC combination set(s) only.
See application file for complete search history.

(56) References Cited

U.S. PATENT DOCUMENTS 6,575,950 B1 * 6/2003  Waksmundzki .. A61F 13/49015
                                                 604/385.11
7,252,658 B2    8/2007  Sayama
(Continued)

FOREIGN PATENT DOCUMENTS

JP     H03-005413 U    1/1991
JP     3122881 U       6/2006
(Continued)

*Primary Examiner* — Bradley H Philips
(74) *Attorney, Agent, or Firm* — Foley & Lardner LLP

(57) ABSTRACT

The present disclosure relates to a diaper with removable waistbands, including a first diaper body disposed in an abdominal area, which is in front on a basis of a waist; removable waistbands, which are connected to both sides of the first diaper body, formed of a stretchable material and configured to be removable by perforated lines formed between the first diaper body and the removable waistbands; waistband Velcro portions provided at ends of the removable waistbands; a second diaper body which is connected to the first diaper body and disposed in a buttocks area, which is in rear on the basis of the waist; combination wings connected to both sides of the second diaper body; combination wing Velcro portions provided at ends of the combination wings; and wrinkle connection portions which connect the first diaper body and the second diaper body in a wrinkle manner.

5 Claims, 10 Drawing Sheets

(56) References Cited

U.S. PATENT DOCUMENTS

| | | | |
|---|---|---|---|
| 8,821,467 B1 | 9/2014 | Minella | |
| 2002/0045879 A1* | 4/2002 | Karami | A61F 13/49015 |
| | | | 604/391 |
| 2002/0111596 A1* | 8/2002 | Fletcher | A61F 13/565 |
| | | | 604/385.03 |
| 2004/0082933 A1* | 4/2004 | Karami | A61F 13/49019 |
| | | | 604/393 |
| 2006/0142729 A1* | 6/2006 | Sivilich | A61F 13/5638 |
| | | | 604/395 |
| 2006/0241558 A1* | 10/2006 | Ramshak | A61F 13/5633 |
| | | | 604/385.09 |
| 2009/0198207 A1* | 8/2009 | Torigoshi | A61F 13/5655 |
| | | | 604/385.29 |
| 2009/0254059 A1* | 10/2009 | Nilsson | A61F 13/496 |
| | | | 604/391 |
| 2014/0163513 A1 | 6/2014 | Schambon | |
| 2016/0250085 A1* | 9/2016 | LaVon | A61F 13/5622 |
| | | | 604/365 |

FOREIGN PATENT DOCUMENTS

| | | |
|---|---|---|
| JP | 2006-204688 | 8/2006 |
| KR | 10-1770398 B1 | 8/2017 |

* cited by examiner

[FIG. 1]
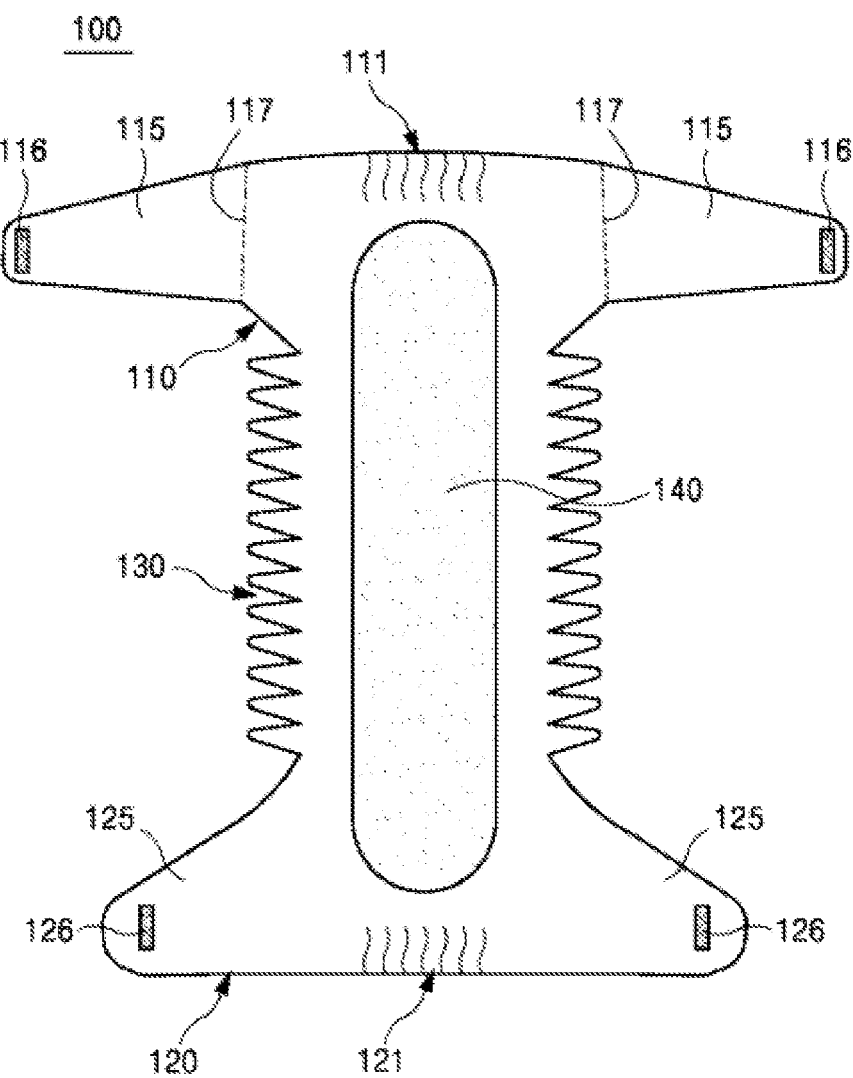

[FIG. 2]
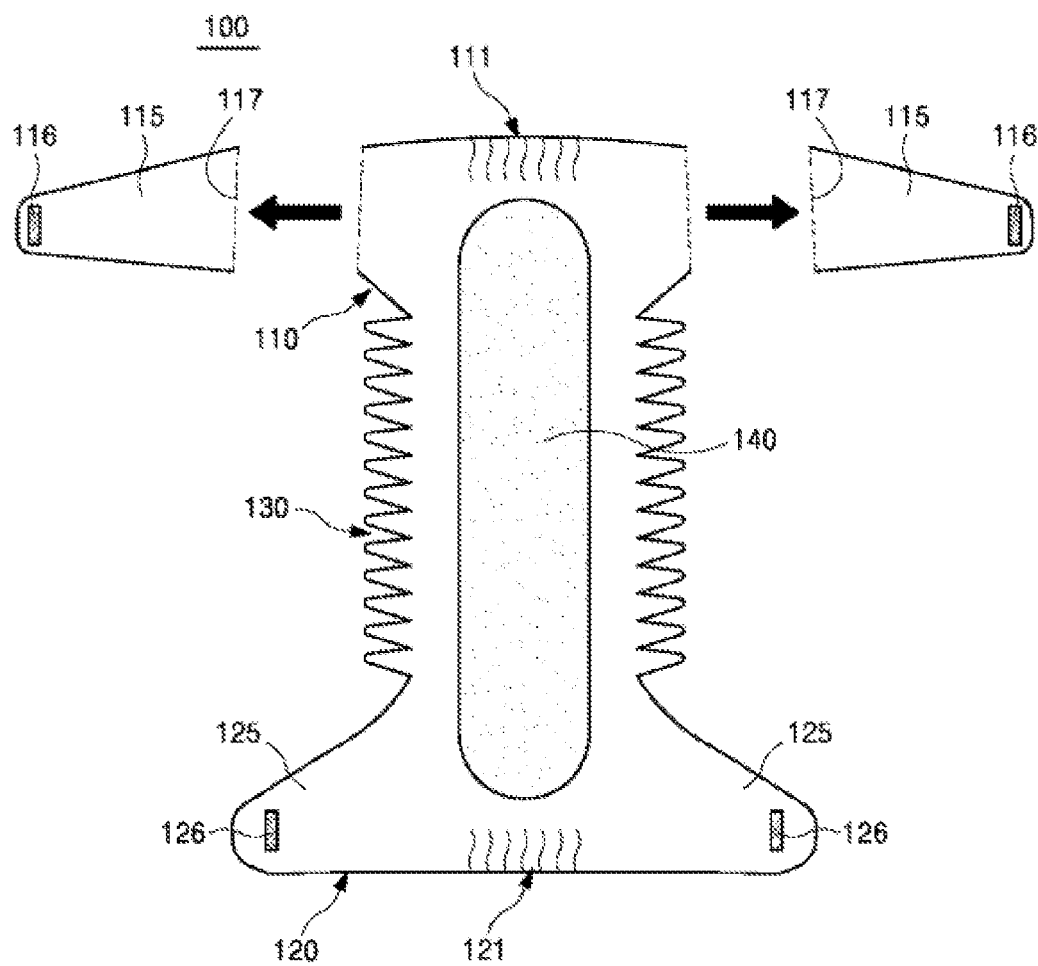

[FIG. 3]
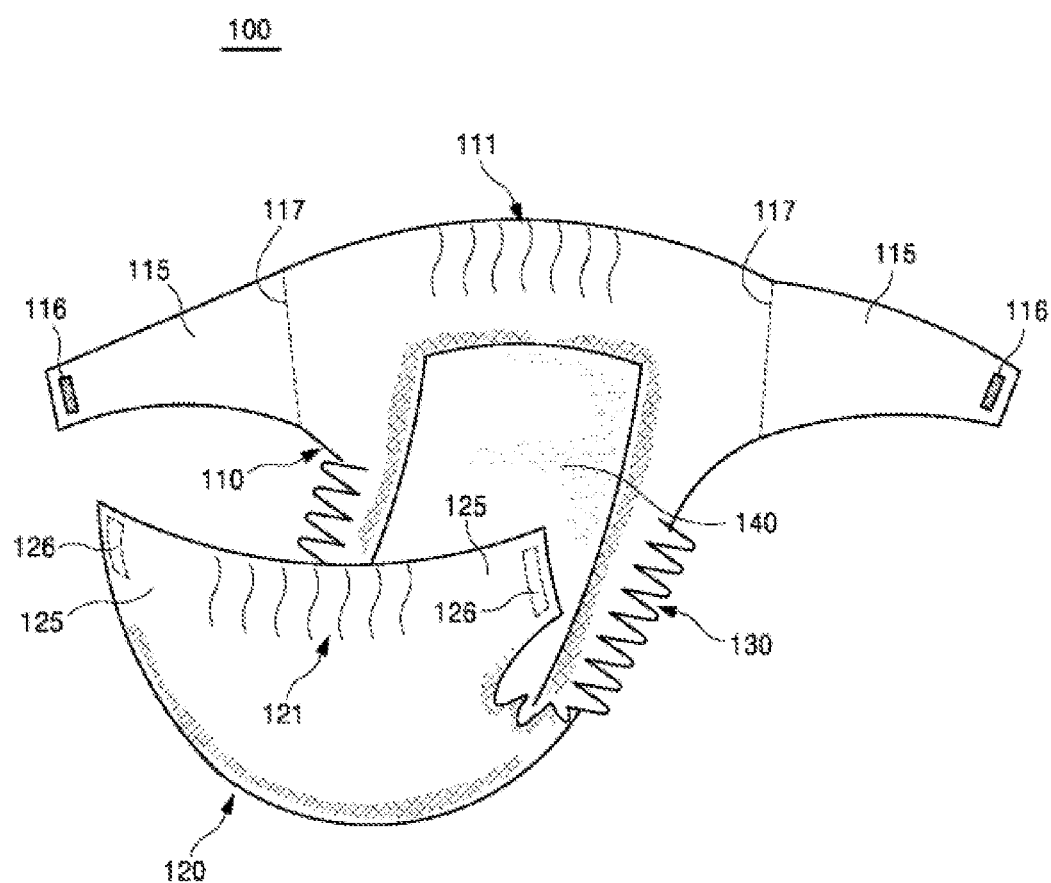

[FIG. 4]
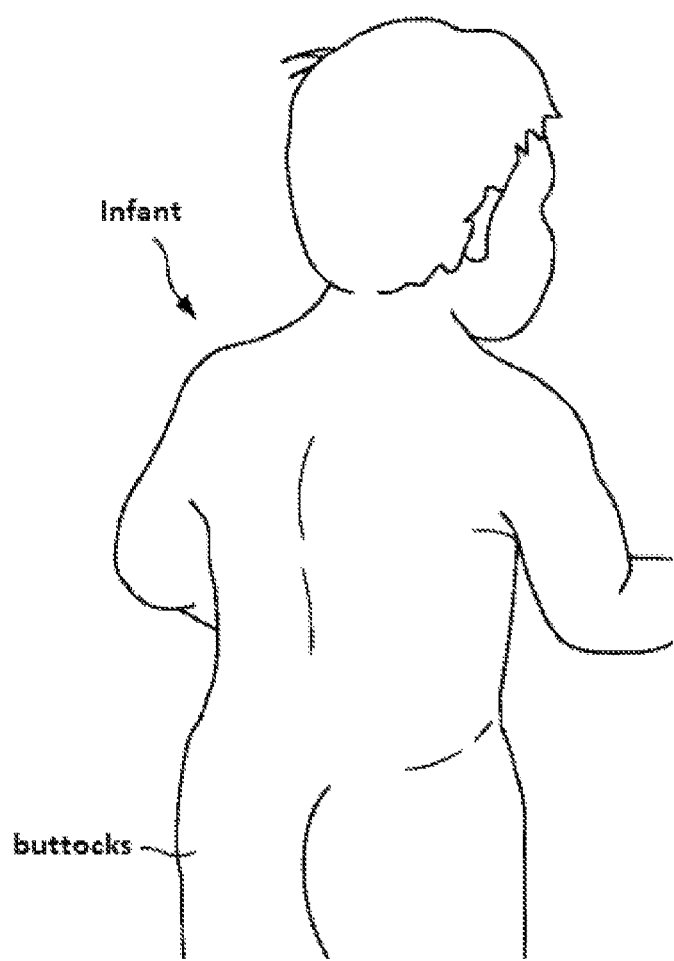

[FIG. 5]
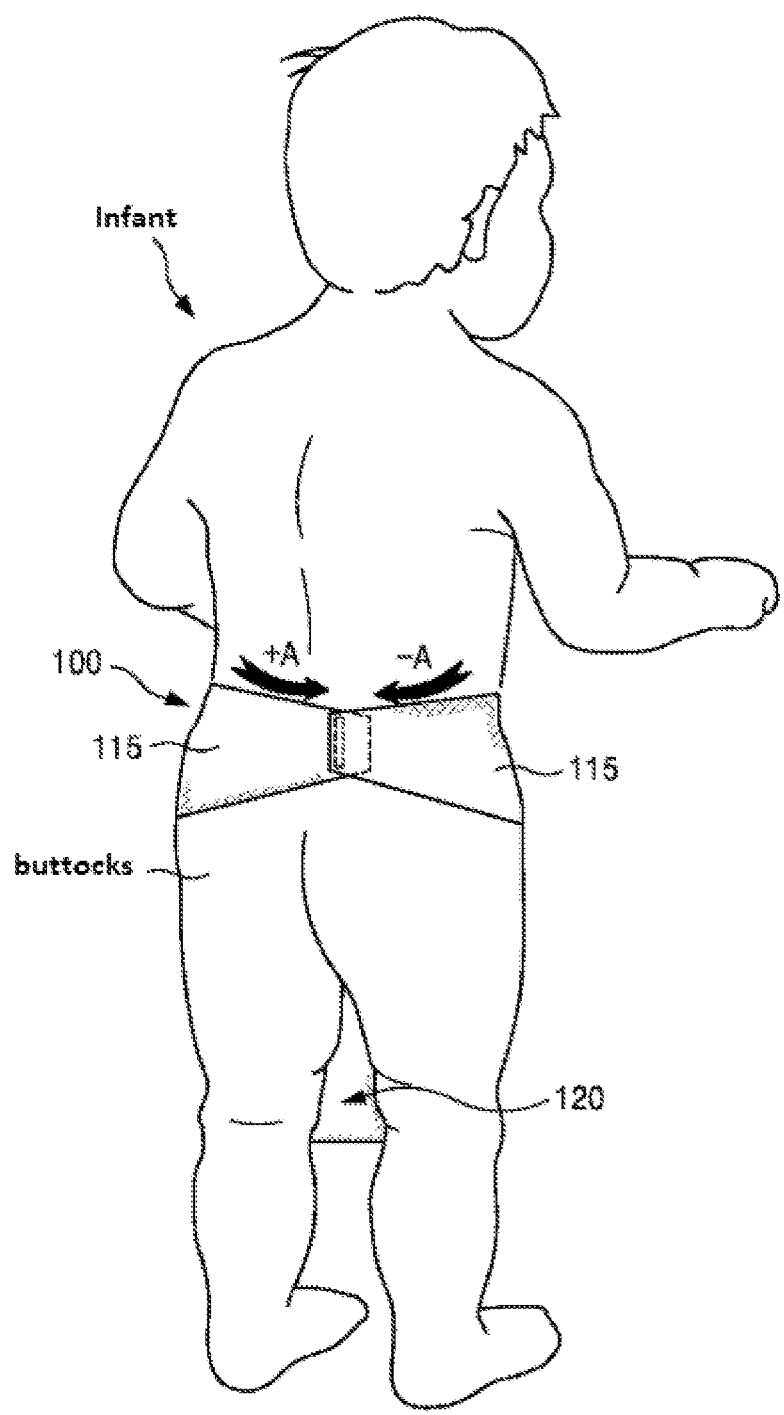

[FIG. 6]
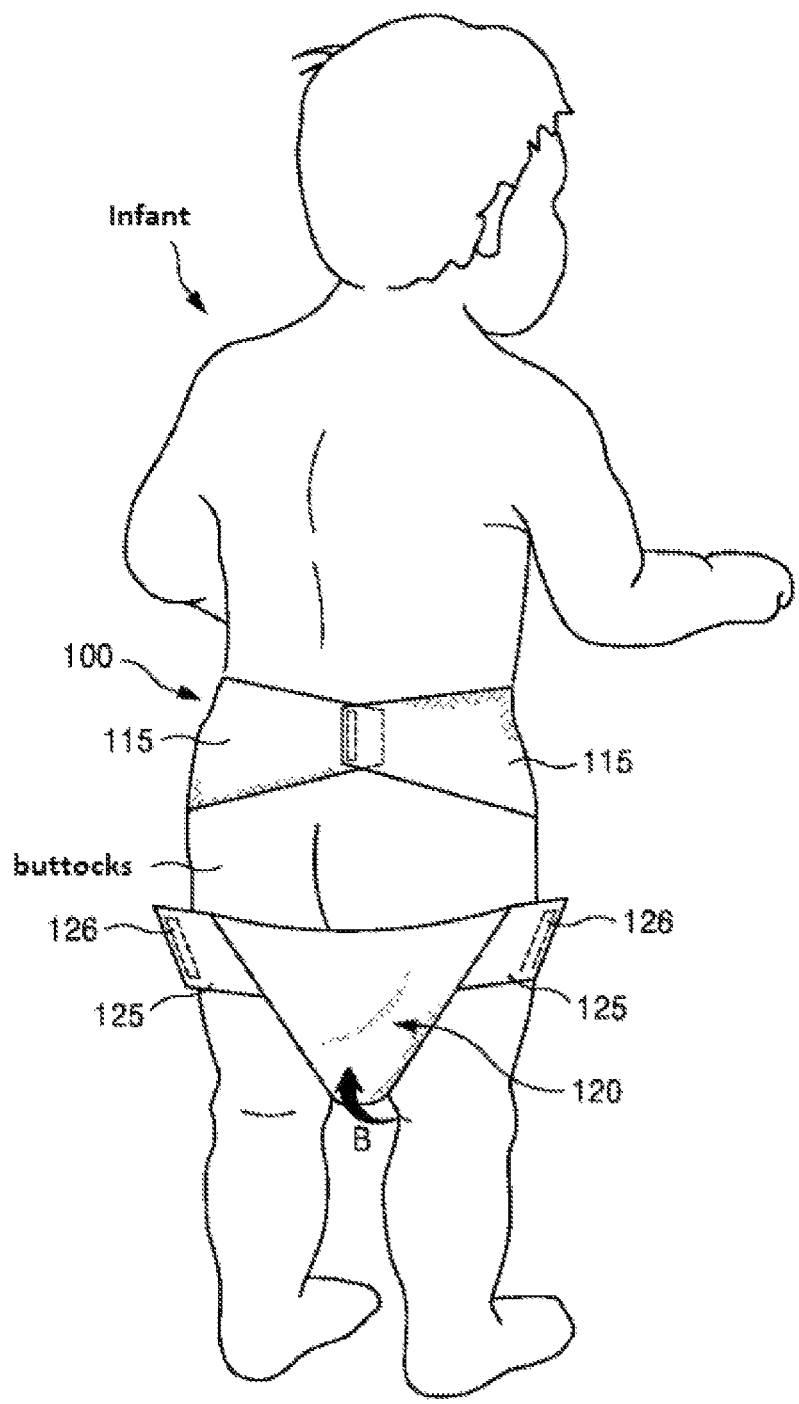

[FIG. 7]
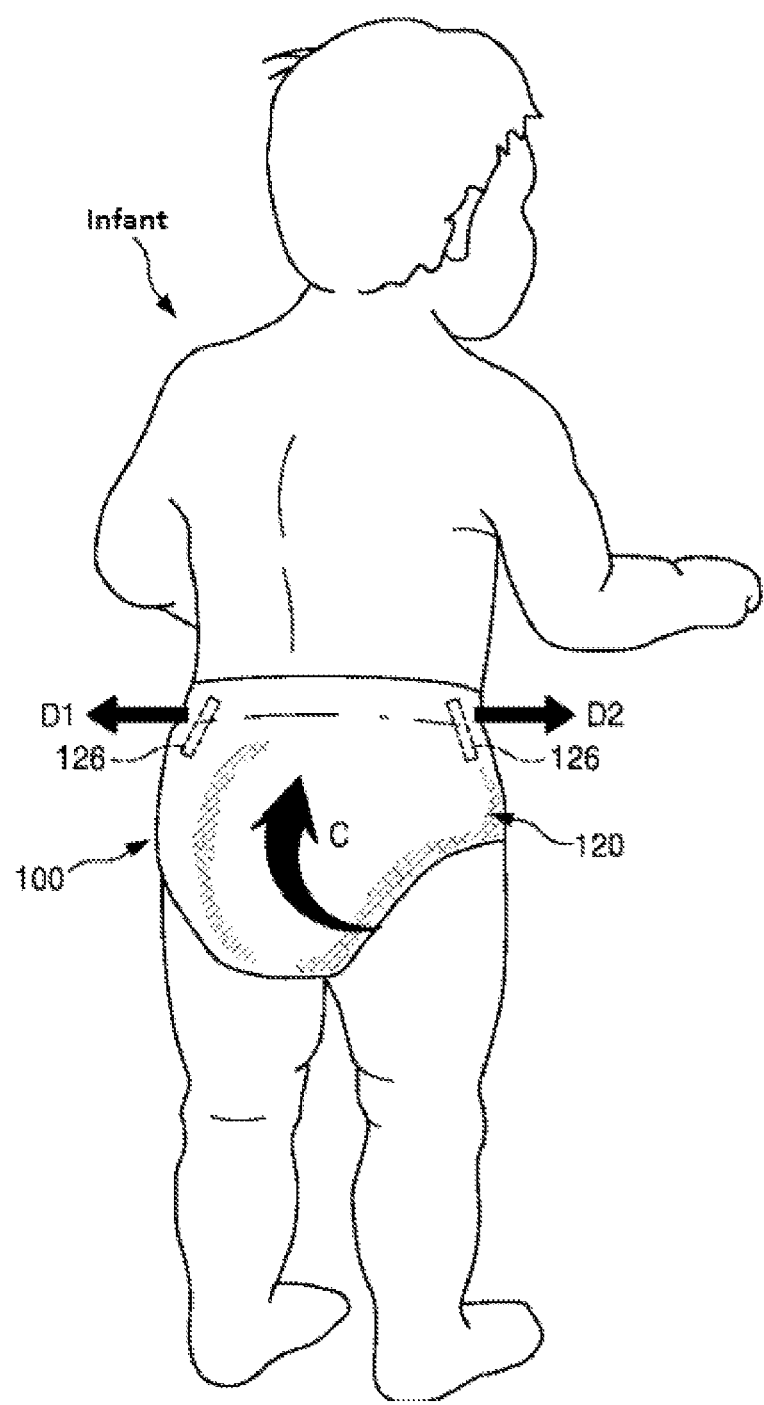

[FIG. 8]
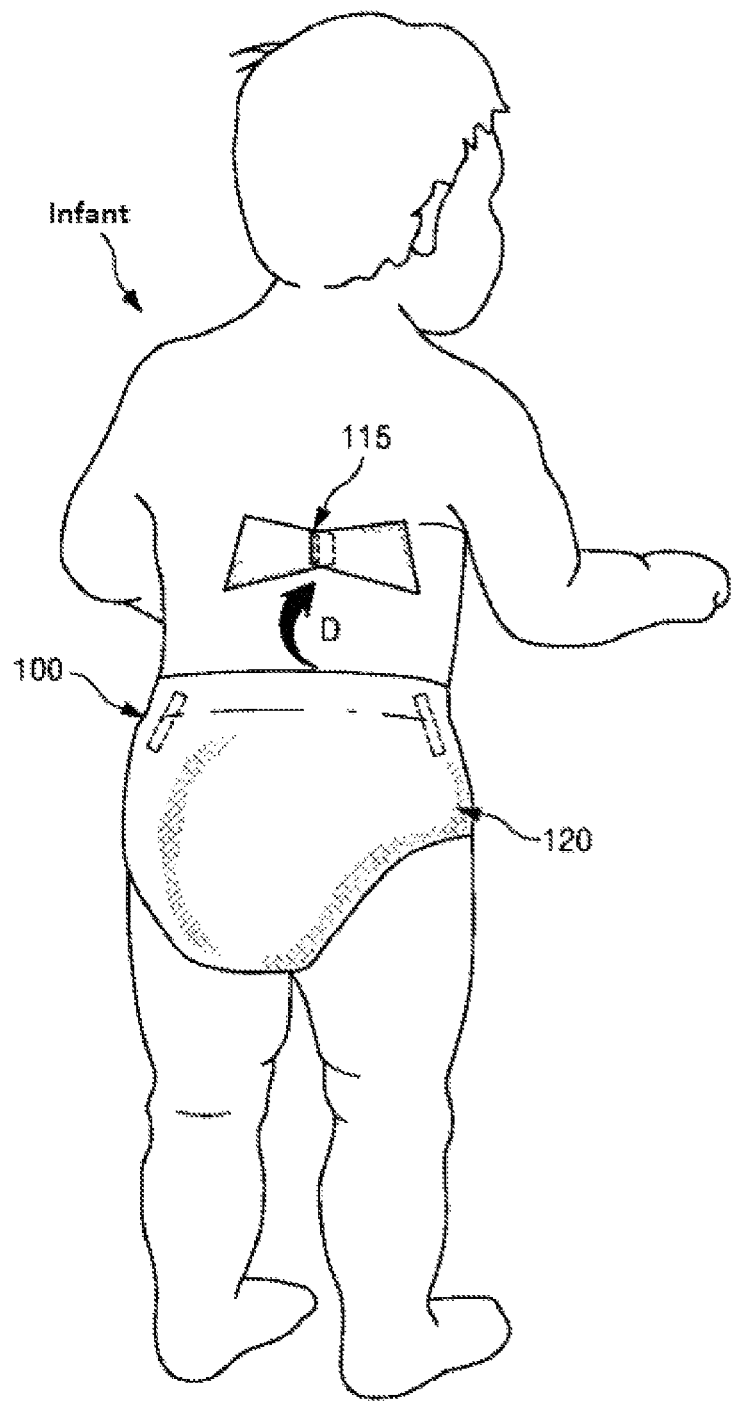

[FIG. 9]
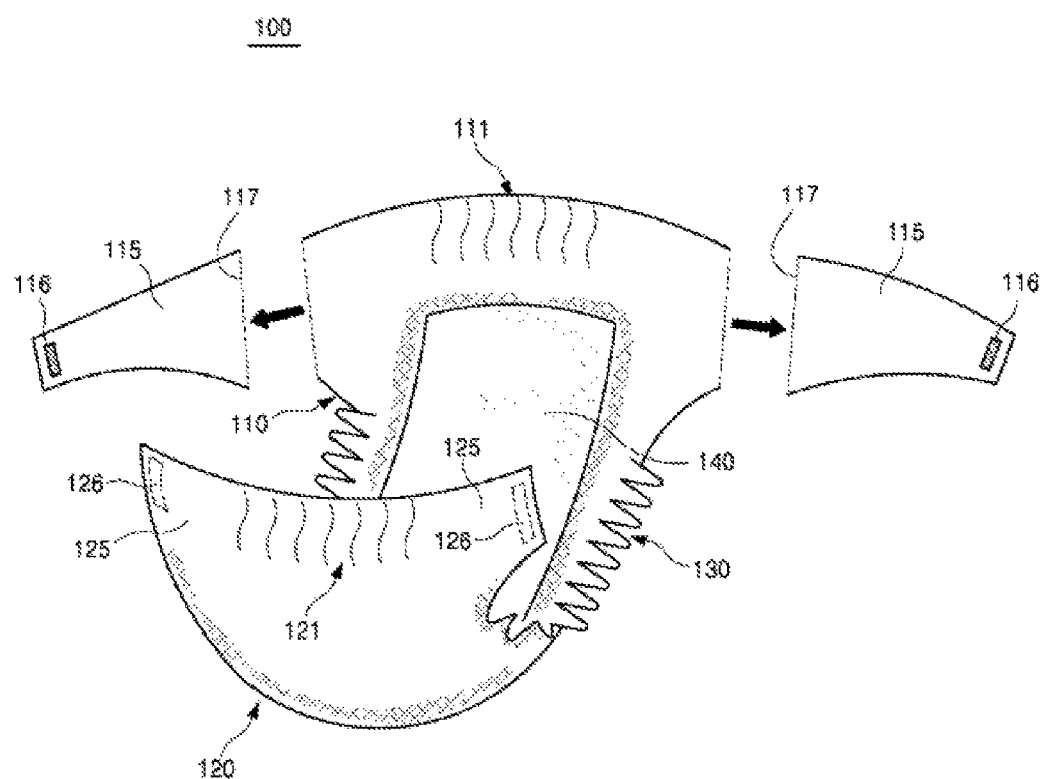

[FIG. 10]
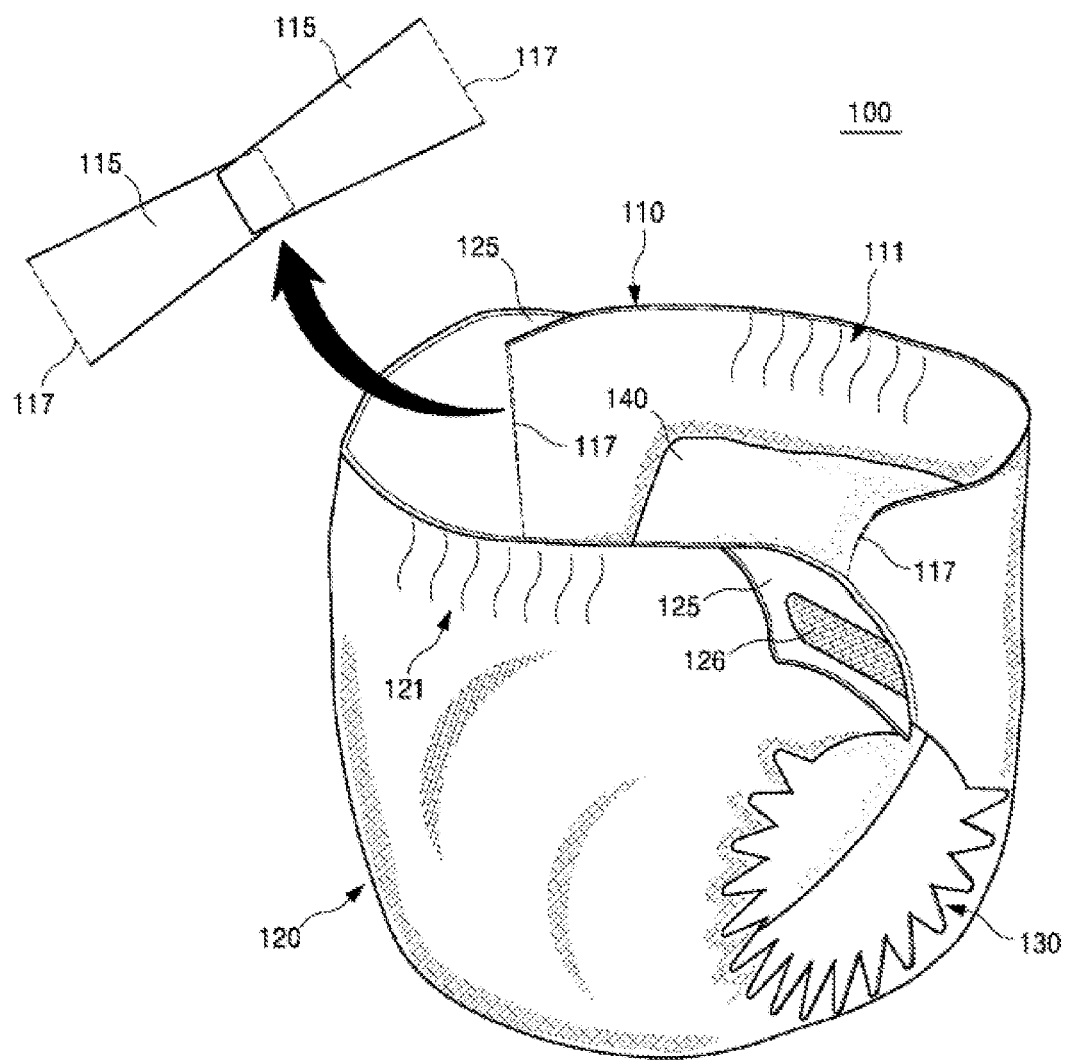

DIAPER INCLUDING REMOVABLE WAISTBAND

CROSS-REFERENCE TO RELATED APPLICATIONS

This application is the National Phase of International Patent Application No. PCT/KR2017/010625, filed Sep. 26, 2017, which claims priority to South Korean Patent Application No. 10-2017-0087105, filed Jul. 10, 2017. The contents of these applications are herein incorporated by reference in their entirety.

TECHNICAL FIELD

The present disclosure relates to a diaper including removable waistbands, and more particularly, a diaper including removable waistbands which may be put on more easily and simply and be removable after being used by applying the removable waistbands so as to prevent occurrences of problems such as air permeability, skin injuries, aesthetics, excrement treatment, etc.

BACKGROUND ART

A diaper serves as an undergarment which absorbs and retains physical excreta such as urine and excrement so as to prevent the excreta from leaking outward and contaminating clothes or other skin.

Typically, diapers are used by 0 to 4-year-old infants and are discarded without reuse after being used once.

Meanwhile, since infants who are one year old or younger lie straight or move less before they are able to walk, it is not too difficult to put conventional diapers on the infants, and most parents prefer general diapers for infants in this period.

However, from around the first birthday when infants start walking, pant diapers which are convenient for putting on are also used in addition to general diapers. Since infants who are one year old or older and have just started walking or running move a great deal due to enormous curiosity and do not understand what is said by adults, it is not easy to allow the infants to wear the general diapers.

Particularly, since participation of fathers in infant care that are poor at caring for infants continuously increases, demand for pant diapers which are convenient to put on has been continuously increasing.

For example, when a conventional diaper is put on an infant, first, while the infant lies straight, feet of the infant are held and his/her buttocks are slightly lifted, and then, the diaper is unfolded and spread under the infant, and both legs of the infant are spread such that one end of the diaper is disposed in front of the infant and fastened to the other end of the diaper by using Velcro portions.

In this case, since a newborn baby lies straight well, it is not difficult to put on a diaper of the baby. However, when an infant just starts walking or running, since the infant intends not to lie still, it is very inconvenient to put on the diaper of the infant.

Also, although it is convenient for a one-year-old infant who starts walking or running to wear a pant diaper in comparison to a general diaper, in consideration of a process of putting on the same, it is inconvenient to take off all bottoms and shoes put on an infant when the pant diaper is to be worn. Particularly, since the infant wears a plurality of bottoms such as undergarments, etc. in cold weather, it is very inconvenient for the infant to wear the pant diaper.

For example, in order to wear a pant diaper on an infant, it is necessary to take off shoes of the infant, take off all bottoms of the infant, such as undergarments, pants, etc., put a pant diaper on the infant, and put on the bottoms and shoes which were taken off again.

In this case, since the infant would not stay still and would continuously move, it is very inconvenient and stressful to the infant to take off and put on clothes and shoes again.

However, since it is necessary to allow an infant to wear a diaper, necessity of loop type diapers which are capable of being more simply and easily put on infants comes to the fore. Accordingly, with respect to this, the present applicant has filed a Korean patent application which has been registered as Korean Patent Registration No. 10-1549985. The registered disclosure (No. 10-1549985) promotes convenience of wearing a diaper by applying a waistband to the diaper. For example, in the above publication, the waistband is called a band portion.

In the case of the registered disclosure owned by the present applicant, although convenience in putting on a diaper may be provided by the waistband, it is pointed out sometimes that problems such as air permeability, skin injuries, aesthetics, wearing, etc. may be caused by the waistband. That is to say, when the waistband is continuously worn, the problems such as air permeability, skin injuries, aesthetics, excrement treatment, wearing, etc. may be caused. Also, while wearing the waistband, inconvenience in wearing may also be caused.

For example, since the waistband comes into contact with skin of an infant, when the waistband is continuously worn, the infant sweats in a waistband area. Here, when the infant plays vigorously or it is in hot weather, the infant sweats more such that the infant feels more confined due to the waistband.

Also, infants, who are more active, may continuously move and crouch or stand. In this process, a shape of the waistband is twisted and folded to form wrinkles such that skin of infants chafes to be injured due to Velcro portions of the waistband which have separated or spread apart.

The waistband which has been twisted and folded to have wrinkles due to vigorous movement of the infant does not look nice aesthetically. Particularly, when the infant repeatedly sits down and stands up, a position of the waistband in contact with a waist is scarcely changed but a diaper body in a buttocks area moves downward. In this case, the waistband hidden by the diaper body is exposed above the diaper body such that the exposed waistband which is twisted and has wrinkles leaves a severely negative impression in a visual or aesthetic aspect.

Also, the waistband provides convenience when a diaper is changed due to urine. However, when a diaper is changed due to excrement, the waistband may be more inconvenient than a conventional diaper.

For example, when the infant sits down and plays on the floor after evacuating a large amount of excrement or even a small amount of excrement, the excrement is moved toward the waistband such that the waistband is stained with the excrement. In this case, since it is necessary to detach waistband Velcro portions in order to change the diaper, inconvenience that his/her mother are smeared with the excrement occurs in her hands.

Also, since mothers believe that wiping to clean up excrement while infants are standing is problematic, treating excrement while infants are lying down is generally preferable. In this process, Velcro portions, etc. at sides of a diaper are detached first, two legs of an infant are held by one hand, the excrement is roughly wiped with the other hand using a front pad of the diaper which is not stained with excrement, the rest of excrement is wiped using wet wipes, etc. and the infant is washed. However, when the infant lies down while wearing the waistband, the waistband is pressurized by the back of the infant such that it becomes more inconvenient to detach the waistband Velcro portions and hands of the mother may be smeared with the excrement of the infant. Accordingly, mothers who treat excrement while infants are lying down may feel more inconvenienced when using the diapers with the waistband than when using general diapers.

Also, mothers who are fearful of the above-described occurrence of the problems such as air permeability, skin injuries, aesthetics, wearing, etc., attempt to initially put waistbands on infants to be as neat as possible without wrinkles. Even here, infants do not stay still and try to move such that it is difficult to neatly put waistbands on infants at once. Due to this, when waistbands Velcro portions are attached or detached several times, inconvenience in wearing may be caused sometimes.

Accordingly, in overall consideration of the above-described problems, necessity for a diaper with a new concept which further increases convenience of putting on diapers due to waistbands and allows the waistbands to be removed after being worn so as to prevent the occurrence of problems such as air permeability, skin injuries, aesthetics, excrement treatment, wearing, etc., comes to the fore.

As related documents, there are the publications of Korean Patent Application Nos. 10-1996-0052868, 10-2000-0000987, 10-2009-0057472, and 10-2009-7009344.

DISCLOSURE OF INVENTION

Technical Problem

The present disclosure is directed to providing a diaper including a removable waistband, and more particularly, a diaper including removable waistbands which may be worn more easily and simply and be removable after being used by applying the removable waistbands so as to prevent occurrence of problems such as air permeability, skin injuries, aesthetics, excrement treatment, etc.

Technical Solution

One aspect of the present disclosure provides a diaper with removable waistbands, including a first diaper body disposed in an abdominal area, which is in front on a basis of a waist; removable waistbands which are connected to both sides of the first diaper body, formed of a stretchable material, and configured to be removable by perforated lines formed between the first diaper body and the removable waistbands; waistband Velcro portions provided at ends of the removable waistbands; a second diaper body which is connected to the first diaper body and disposed in a buttocks area in the rear on the basis of the waist; combination wings connected to both sides of the second diaper body, combination wing Velcro portions provided at ends of the combination wings; and wrinkled connection portions which connect the first diaper body to the second diaper body in a wrinkled manner.

The first diaper body may include a first elastic expansion portion configured to elastically expand the first diaper body. Also, the second diaper body may include a second elastic expansion portion configured to elastically expand the second diaper body. The first diaper body, the wrinkle connection portions, and the second diaper body may include excreta absorption pads.

Advantageous Effects

According to the present disclosure, an effect of preventing occurrence of problems such as air permeability, skin injuries, aesthetics, etc. by applying removable waistbands to a diaper so as to not only be more easily and simply worn but also be removable after being used is provided.

BRIEF DESCRIPTION OF DRAWINGS

FIG. 1 is a plan view of a configuration of a diaper with removable waistbands according to one embodiment of the present disclosure.

FIG. 2 is a view of illustrating a state in which the removable waistbands are removed from FIG. 1.

FIG. 3 is a perspective view of the diaper with the removable waistbands, which is shown in FIG. 1, according to one embodiment of the present disclosure.

FIG. 4 shows an appearance of an infant from behind.

FIGS. 5 to 8 are views of illustrating operations of a process of putting the diaper with the removable waistbands on the infant in FIG. 4.

FIG. 9 is a view of illustrating a state in which the diaper with the removable waistbands is used as a band type diaper, according to one embodiment of the present disclosure.

FIG. 10 is a view of illustrating a state in which the diaper with the removable waistbands is used as a pant diaper, according to one embodiment of the present disclosure.

MODE FOR INVENTION

Advantages and features of the present disclosure and a method of achieving the same will become apparent with reference to the attached drawings and embodiments described in detail below.

However, the present disclosure is not limited to the following embodiments and may be embodied in a variety of different modifications.

In the specification, the embodiments are provided to completely disclose the present disclosure and to allow one of ordinary skill in the art to completely understand the scope of the present disclosure. Also, the present disclosure will be defined by the scope of the claims.

Accordingly, in some embodiments, well-known components, well-known operations, and well-known technologies will not be described in detail to avoid obscuring understanding of the present disclosure.

Throughout the specification, like reference numerals refer to like elements. Also, the terms used (stated) herein are for explaining embodiments but are not intended to limit the present disclosure.

Throughout the specification, unless particularly defined otherwise, singular forms include plural forms. Also, components and operations (actions) stated with "comprising (or including)" will not exclude presence or addition of one or more other components and operations.

Unless defined otherwise, all the terms (including technical and scientific terms) used in the specification may be used as meanings understood in common by one of ordinary skill in the art.

Also, terms such as those defined in commonly used dictionaries should not be interpreted in an idealized or excessively formal sense unless defined otherwise.

Hereinafter, exemplary embodiments of the present disclosure will be described with reference to the attached drawings.

FIG. 1 is a plan view of a configuration of a diaper with removable waistbands according to one embodiment of the present disclosure. FIG. 2 is a view of illustrating a state in which the removable waistbands are removed from FIG. 1. FIG. 3 is a perspective view of the diaper with removable waistbands according to one embodiment of the present disclosure which is shown in FIG. 1, and FIG. 4 shows an appearance of an infant from behind. FIGS. 5 to 8 are views of illustrating operations of a process of allowing the infant of FIG. 4 to wear the diaper with removable waistbands.

Referring to the above drawings, a diaper 100 with removable waistbands according to the embodiment of the present disclosure may be worn more easily and simply and be removed after being used with removable waistbands 115 such that problems such as air permeability, skin damage, aesthetics, excrement treatment, etc. may be prevented.

The diaper 100 with the removable waistbands may include a first diaper body 110, a second diaper body 120, and a wrinkle connection portion 130.

Meanwhile, in the embodiment, for convenience of explanation, the first diaper body 110, the second diaper body 120, and the wrinkle connection portion 130 will be separately described but may be integrally manufactured as a whole or may be partially connected to each other.

For example, the wrinkle connection portion 130 may be one component of the second diaper body 120 which is formed at an end of the second diaper body 120.

Although a diaper wearer may generally be an infant as shown in FIG. 4, an adult, for example, a patient with reduced mobility, etc. or a companion animal, such as a pet dog, etc., may wear a diaper.

Accordingly, the diaper 100 with the removable waistbands according to the embodiment of the present disclosure may include both an adult-type diaper and a companion animal-type as well as an infant-type diaper. However, hereinafter, an infant-type diaper will be described for convenience of explanation.

To describe a structure of the diaper 100 with the removable waistbands according to the embodiment of the present disclosure in detail, first, the first diaper body 110 is a part disposed in an abdominal area, which is in front on the basis of a waist.

That is, when it is intended to put the diaper 100 on an infant from behind as shown in FIG. 4, the first diaper body 110 may be disposed in the abdominal area, that is, a front side of the infant.

Unlike the drawings, when it is intended to put the diaper 100 on the infant from the front, the first diaper body 110 may be disposed in a buttocks area and the second diaper body 120 may be disposed in the abdominal area. Accordingly, a wearing direction is irrelevant to the present disclosure.

The first diaper body 110 may include a first elastic expansion portion 111 for elastically expanding the first diaper body 110. The first elastic expansion portion 111 may be formed by backstitching a band. Although it is convenient when the first elastic expansion portion 111 is provided, it may not be necessary to provide the first elastic expansion portion 111. Accordingly, the scope of the present disclosure is not limited thereto.

Meanwhile, the first diaper body 110 includes the removable waistbands 115. The removable waistbands 115 are a type of disposable adhesive wings which are connected to both sides of the first diaper body 110 and are formed of a stretchable material and provided to be removable by perforated lines 117 formed between the removable waistbands 115 and the first diaper body 110.

In detail, in this embodiment, a pair of the removable waistbands 115 are provided to be symmetrical to each other on both sides of the first diaper body 110.

In terms of a developmental state and a waist size which differ for each infant, the removable waistbands 115 may be formed of a stretchable elastic material but are not limited thereto. The removable waistbands 115 include waistband Velcro portions 116 provided at ends thereof.

Since the removable waistbands 115 are connected to the first diaper body 110 by the perforated lines 117, as shown in FIGS. 1 and 2, when the removable waistbands 115 are pulled, the removable waistbands 115 may be easily separated and removed from the first diaper body 110. As a result, when the removable waistbands 115 are fastened once, the diaper 100 was completely worn, and then the removable waistbands 115 may be removed from the diaper 100.

Next, the second diaper body 120 is connected to the first diaper body 110 and is a part disposed in the buttocks area in the rear on the basis of the waist.

As shown in FIG. 7, the second diaper body 120 is stably disposed while surrounding the buttocks area. That is to say, after the diaper 100 with the removable waistbands according to the embodiment of the present disclosure is put on, only the second diaper body 120 may be seen when viewed from behind as shown in FIG. 7.

A pair of combination wings 125 are provided on both sides of the second diaper body 120. Also, the combination wings 125 include combination wing Velcro portions 126 provided at ends thereof.

Each of the combination wing Velcro portions 126 formed on the combination wings 125 are attached to the first diaper body 110 such that the first diaper body 110 and the second diaper body 120 are connected to each other. That is to say, the second diaper body 120 may be disposed at the buttocks area of the infant through a space between legs of the infant in front of the infant and then may be combined with the first diaper body 110 through the combination wing Velcro portions 126 of the combination wings 125.

The second diaper body 120 may also include a second elastic expansion portion 121 for elastically expanding the second diaper body 120. The second elastic expansion portion 121 may also be formed by backstitching a band. The second elastic expansion portion 121 is also an optional part.

Next, the wrinkle connection portion 130 is a part which connects the first diaper body 110 and the second diaper body 120 in a wrinkled manner.

The diaper 100 with the removable waistbands according to this embodiment of the present disclosure may be reduced in size when being folded but may increase in size when being used due to formation of the wrinkle connection portion 130.

Lastly, an excreta-absorption pad 140 is a pad which is disposed over the first diaper body 110, the wrinkle connection portion 130, and the second diaper body 120. The excreta-absorption pad 140 may be an integrated type or may be separately manufactured and attached to a corresponding position.

Although the first diaper body 110, the wrinkle connection portion 130, and the second diaper body 120 are also formed of a cloth, non-woven fabric, or the like which is harmless to a human body, such materials may not absorb and retain excreta substantially, such as urine and excrement.

Accordingly, the excreta-absorption pad 140 is provided on the first diaper body 110, the wrinkle connection portion 130, and the second diaper body 120 so as to absorb and retain excreta, such as urine and excrement.

Hereinafter, a method of putting on the diaper 100 with the removable waistbands will be described with reference to FIGS. 4 to 8.

When the infant has been turned around as shown in FIG. 4, the first diaper body 110 is disposed in the abdominal area of the infant and then the pair of removable waistbands 115 surround the buttocks (in directions +A and −A in FIG. 5) and are connected to each other by the waistband Velcro portions 116 provided on the removable waistbands 115. In this case, since the removable waistbands 115 are objects which should be immediately removed after the diaper is completely worn, it is necessary only to attach the removable waistbands for a while for convenience of wearing without being concerned about attaching positions of the waistband Velcro portions 116 or shapes of the removable waistbands 115 being connected to each other. As such, without inconvenience of attaching or detaching general waistbands to dispose the waistbands well while worrying about problems such as air permeability, skin injuries, aesthetics, etc., it is only necessary to simply connect the waistbands at once.

Then, due to the pair of removable waistbands 115, the diaper 100 is put on a waist part of the infant first. This state is shown in FIG. 5.

Next, in a direction of an arrow B as shown in FIG. 6, the second diaper body 120 is taken out through the space between the legs of the infant toward the buttocks of the infant.

Then, as shown in FIG. 7, the second diaper body 120 is lifted in a direction of an arrow C to surround the buttocks and then the combination wings 125 provided on the both sides of the second diaper body 120 are pulled in directions of arrows D1 and D2 and combined with the first diaper body 110 by using the combination wing Velcro portions 126.

As described above, when the combination wings 125 provided on the both sides of the second diaper body 120 are combined with the first diaper body 110, the removable waistbands 115 are hidden by the second diaper body 120 so as to not be seen as shown in FIG. 7. However, the removable waistbands 115 are surrounding the waist of the infant.

In this state, as shown in FIG. 8, a hand is put into the second diaper body 120 and the removable waistbands 115 are pulled.

When the removable waistbands 115 are pulled, the perforated lines 117 are torn out by a pulling force such that the removable waistbands 115 may be separated and removed from the first diaper body 110.

When the removable waistbands 115 are removed as described above, since factors which surround and pressurize the waist disappear, it is possible to prevent occurrence of the problems such as air permeability, skin injuries, aesthetics, etc. That is, a case shown in FIG. 8 has a shape similar to a case in which an infant is laid down and a general diaper is put on.

As a result, the removable waistbands 115 perform a function of allowing the diaper 100 to be easily put on and then are removed such that it is possible to prevent the problems such as air permeability, skin injuries, aesthetics, etc., which may occur as the removable waistbands 115 are continuously worn.

According to this embodiment of the present disclosure including the above-described structure and operations, the diaper may not only be easily and simply worn by applying the removable waistbands 115 but also be removable after being used such that it is possible to prevent occurrence of the problems such as air permeability, skin injuries, aesthetics, excrement treatment, etc.

Effects of the present disclosure will be further described. That is, when the diaper 100 according to the embodiment of the present disclosure is used, it is unnecessary to lay down an infant who is standing. Also, since there is no inconvenience of taking off all bottoms and shoes of an infant like a pant diaper in the diaper 100 according to the embodiment of the present disclosure, it is possible to prevent an infant from being stressed. Also, parents may conveniently put the diaper 100 with the removable waistbands on the infant while the infant is standing, which greatly aids in infant care.

Actually, in consideration of changing ten or more diapers in a day, when the method according to the embodiment of the present disclosure is applied, it is expected that a great deal of convenience may be provided to parents.

Particularly, in comparison to a general pant diaper, it is very convenient to use the diaper 100 with the removable waistbands according to the embodiment of the present disclosure. Actually, pant diapers are more inconvenient than expected. That is to say, in the case of pant diapers, although putting them on is expected to be convenient, it is necessary but inconvenient to take off all bottoms put on an infant, put a pant diaper on the infant, and to put clothes on again.

However, it is possible to conveniently and quickly put the diaper 100 with the removable waistbands according to the embodiment of the present disclosure on an infant without completely removing clothes of the infant, which is very convenient.

According to the diaper 100 with the removable waistbands according to the embodiment of the present disclosure which includes the above-described structure and operations, it is possible to more simply and easily put the diaper on an infant.

Meanwhile, FIG. 9 is a view of illustrating a state in which the diaper with the removable waistbands is used as a band type diaper, according to one embodiment of the present disclosure, and FIG. 10 is a view of illustrating a state in which the diaper with removable waistbands is used as a pant diaper, according to one embodiment of the present disclosure.

Parents do not use only one type of diapers and have both general diapers and pant diapers as necessary. This is because it is necessary to select a type of diaper to use depending on a variety of infant-care environments and situations.

For example, when the removable waistbands 115 are removed along the perforated lines 117 while both of the Velcro portions are connected, the diaper 100 with the removable waistbands may be used as a pant diaper as shown in FIG. 10.

Also, when all the Velcro portions are separated and the removable waistbands 115 are removed along the perforated lines 117, the diaper 100 may be used as a general diaper, that is, a band type as shown in FIG. 9.

In other words, the diaper 100 with the removable waistbands according to the embodiment of the present disclosure is a 3-in-1 multi-functional diaper which is modifiable into a pant diaper (see FIG. 10) or a general diaper (see FIG. 9) depending on a variety of infant-care environments and situations. That is, the diaper 100 with the removable waistbands according to the embodiment of the present disclosure may be a 3-in-1 multi-functional diaper capable of being used as three types of diapers, that is, a loop type diaper, a band type diaper, and a pant diaper as shown in FIGS. 3, 9, and 10.

Accordingly, it is unnecessary for parents to have separate pant diapers or general diapers to correspond to a variety of infant-case environments and situations, and it is necessary for parents to have only the diaper 100 with removable waistbands according to the embodiment of the present disclosure.

As described above, the present disclosure is not limited to the above-described embodiment and it is obvious to one of ordinary skill in the art that a variety of changes and modifications may be made without departing from the concept and scope of the present disclosure. Accordingly, changed examples or modified examples should be included in the claims of the present disclosure.

<Description of Reference Numerals>

| | |
|---|---|
| 100: diaper | 110: first diaper body |
| 111: first elastic expansion portion | 115: removable waistband |
| 116: waistband Velcro portion | 117: perforated line |
| 120: second diaper body | 121: second elastic expansion portion |
| 125: combination wing | 126: combination wing Velcro portion |
| 130: wrinkle connection portion | 140: excreta absorption pad |

The invention claimed is:

1. A diaper with removable waistbands, comprising:
a first diaper body configured to be disposed in an abdominal area, which is in front on a basis of a waist;
removable waistbands, which are connected to both sides of the first diaper body via perforated lines formed between the first diaper body and the removable waistbands, formed of a stretchable material and configured to be removable by tearing out the perforated lines;
waistband hook fastener portions provided at ends of the removable waistbands;
a second diaper body which is connected to the first diaper body and configured to be disposed in a buttocks area, which is in rear on a basis of the waist;
combination wings connected to both sides of the second diaper body;
combination wing hook fastener portions provided at ends of the combination wings; and
wrinkle connection portions which connect the first diaper body and the second diaper body in a wrinkle manner.

2. The diaper of claim 1, wherein the first diaper body comprises a first elastic expansion portion configured to elastically expand the first diaper body,
wherein the second diaper body comprises a second elastic expansion portion configured to elastically expand the second diaper body, and
wherein the first diaper body, the wrinkle connection portions, and the second diaper body comprise an excreta absorption pad.

3. The diaper of claim 1, wherein the waistband hook fastener portions are connectable to each other.

4. The diaper of claim 1, wherein the removable waistbands are connectable to each other via the waistband hook fastener portions.

5. The diaper of claim 1, wherein
the removable waistbands are connectable to each other, and
the removable waistbands in a connected form are removable from the first diaper body.

* * * * *